United States Patent
Mazor et al.

(10) Patent No.: US 7,649,978 B2
(45) Date of Patent: Jan. 19, 2010

(54) AUTOMATED SELECTION OF X-RAY REFLECTOMETRY MEASUREMENT LOCATIONS

(75) Inventors: Isaac Mazor, Haifa (IL); Alex Dikopoltsev, Haifa (IL); Boris Yokhin, Nazareth Illit (IL); Dileep Agnihotri, Round Rock, TX (US); Tzachi Rafaeli, Givat Shimshit (IL); Alex Tokar, Haifa (IL); David Berman, Kiryat Tivon (IL); Moshe Beylin, Nahariya (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 0 days.

(21) Appl. No.: 12/232,259

(22) Filed: Sep. 12, 2008

(65) Prior Publication Data
US 2009/0074141 A1 Mar. 19, 2009

Related U.S. Application Data

(63) Continuation of application No. 11/798,617, filed on May 15, 2007, now abandoned.

(60) Provisional application No. 60/800,589, filed on May 15, 2006.

(51) Int. Cl.
*G01B 15/02* (2006.01)
(52) U.S. Cl. .............................. 378/90; 378/86; 378/89
(58) Field of Classification Search .............. 378/70–90
See application file for complete search history.

(56) References Cited

U.S. PATENT DOCUMENTS

| | | |
|---|---|---|
| 3,980,568 A | 9/1976 | Pitchford et al. |
| 4,446,568 A | 5/1984 | Williams et al. |
| 4,725,963 A | 2/1988 | Taylor et al. |
| 4,847,882 A | 7/1989 | Knoth et al. |
| 4,916,720 A | 4/1990 | Yamamoto et al. |
| 4,989,226 A | 1/1991 | Woodbury et al. |

(Continued)

FOREIGN PATENT DOCUMENTS

WO  WO 01/24200  4/2001

(Continued)

OTHER PUBLICATIONS

Dane et al., "Application of Genetic Algorithms for Characterization of Thin Layered Materials by Glancing Incidence X-Ray Reflectometry", Physica B 253 (1998) 254-268.

(Continued)

*Primary Examiner*—Jurie Yun
(74) *Attorney, Agent, or Firm*—Smith, Gambrell & Russell, LLP

(57) ABSTRACT

The computer-implemented method for inspection of a sample includes defining a plurality of locations on a surface of the sample, irradiating the surface at each of the locations with a beam of X-rays, and measuring an angular distribution of the X-rays that are emitted from the surface responsively to the beam, so as to produce a respective plurality of X-ray spectra. The X-ray spectra are analyzed to produce respective figures-of-merit indicative of a measurement quality of the X-ray spectra at the respective location. One or more locations are selected out of the plurality of locations responsively to the figures-of-merit, and a property of the sample is estimated using the X-ray spectra measured at the selected location.

20 Claims, 5 Drawing Sheets

U.S. PATENT DOCUMENTS

| | | | |
|---|---|---|---|
| 5,151,588 | A | 9/1992 | Kiri et al. |
| 5,481,109 | A | 1/1996 | Ninomiya et al. |
| 5,574,284 | A | 11/1996 | Farr |
| 5,619,548 | A | 4/1997 | Koppel |
| 5,740,226 | A | 4/1998 | Komiya et al. |
| 5,900,645 | A | 5/1999 | Yamada |
| 5,923,720 | A | 7/1999 | Barton et al. |
| 5,937,026 | A | 8/1999 | Satoh |
| 5,949,847 | A | 9/1999 | Terada et al. |
| 5,963,329 | A | 10/1999 | Conrad et al. |
| 6,041,095 | A | 3/2000 | Yokhin |
| 6,041,098 | A | 3/2000 | Touryanski et al. |
| 6,108,398 | A | 8/2000 | Mazor et al. |
| 6,192,103 | B1 | 2/2001 | Wormington et al. |
| 6,226,347 | B1 | 5/2001 | Golenhofen |
| 6,226,349 | B1 | 5/2001 | Schuster et al. |
| 6,351,516 | B1 | 2/2002 | Mazor et al. |
| 6,381,303 | B1 | 4/2002 | Vu et al. |
| 6,389,102 | B2 | 5/2002 | Mazor et al. |
| 6,453,002 | B1 | 9/2002 | Mazor et al. |
| 6,453,006 | B1 | 9/2002 | Koppel et al. |
| 6,507,634 | B1 | 1/2003 | Koppel et al. |
| 6,512,814 | B2 | 1/2003 | Yokhin et al. |
| 6,556,652 | B1 | 4/2003 | Mazor et al. |
| 6,639,968 | B2 | 10/2003 | Yokhin et al. |
| 6,643,354 | B2 | 11/2003 | Koppel et al. |
| 6,680,996 | B2 | 1/2004 | Yokhin et al. |
| 6,704,661 | B1 | 3/2004 | Opsal et al. |
| 6,711,232 | B1 | 3/2004 | Janik |
| 6,744,850 | B2 | 6/2004 | Fanton et al. |
| 6,744,950 | B2 | 6/2004 | Aleksoff |
| 6,750,952 | B2 | 6/2004 | Grodnensky et al. |
| 6,754,304 | B1 | 6/2004 | Kumakhov |
| 6,754,305 | B1 | 6/2004 | Rosencwaig et al. |
| 6,771,735 | B2 | 8/2004 | Janik et al. |
| 6,810,105 | B2 | 10/2004 | Nasser-Ghodsi et al. |
| 6,823,043 | B2 | 11/2004 | Fewster et al. |
| 6,895,075 | B2 | 5/2005 | Yokhin et al. |
| 6,947,520 | B2 | 9/2005 | Yokhin et al. |
| 6,977,986 | B1 | 12/2005 | Beanland et al. |
| 7,023,954 | B2 | 4/2006 | Rafaeli et al. |
| 7,062,013 | B2 | 6/2006 | Berman et al. |
| 7,068,753 | B2 | 6/2006 | Berman et al. |
| 7,071,007 | B2 | 7/2006 | Tseng et al. |
| 7,103,142 | B1 * | 9/2006 | Agnihotri et al. ............. 378/82 |
| 7,110,491 | B2 | 9/2006 | Mazor et al. |
| 7,120,228 | B2 | 10/2006 | Yokhin et al. |
| 7,130,376 | B2 | 10/2006 | Berman et al. |
| 7,245,695 | B2 | 7/2007 | Mazor et al. |
| 2001/0028699 | A1 | 10/2001 | Iwasaki |
| 2001/0043668 | A1 | 11/2001 | Hayashi et al. |
| 2002/0097837 | A1 | 7/2002 | Fanton et al. |
| 2002/0110218 | A1 | 8/2002 | Koppel et al. |
| 2003/0012337 | A1 | 1/2003 | Fewster et al. |
| 2003/0128809 | A1 | 7/2003 | Umezawa et al. |
| 2003/0157559 | A1 | 8/2003 | Omote et al. |
| 2004/0052330 | A1 | 3/2004 | Koppel et al. |
| 2004/0109531 | A1 | 6/2004 | Yokhin et al. |
| 2004/0131151 | A1 | 7/2004 | Berman et al. |
| 2004/0156474 | A1 | 8/2004 | Yokhin et al. |
| 2004/0218717 | A1 | 11/2004 | Koppel et al. |
| 2004/0267490 | A1 | 12/2004 | Opsal et al. |
| 2006/0062351 | A1 | 3/2006 | Yokhin et al. |
| 2008/0021665 | A1 * | 1/2008 | Vaughnn ..................... 702/84 |

OTHER PUBLICATIONS

T.C. Huang, "Characterization of Single-and Multiple-Layer Films by X-Ray Reflectometry", Advances in X-Ray Analysis, vol. 35, pp. 137-142, 1992.

Kozaczek, et al., "X-ray Diffraction Metrology for 200 mm Process Qualification and Stability Assessment", Advanced Metallization Conference (Montreal, Canada, Oct. 8-11, 2001.

An English abstract of JP 10 318949, Dec. 4, 1998.

A R Powell, et al., "X-ray diffraction and reflectivity characterization of SiGe superlattice structures", Semicond. Sci. Technol. 7 (1992) 627-631, 1992.

Lengeler, "X-ray reflection, A new tool for investigating layered structures and interfaces", Advances in X-ray Analysis 35 (1992), p. 127.

Lankosz, et al., "Research in quantitative X-ray fluorescence microanalysis of patterned thin films", Advances in X-ray Analysis 43 (1999), pp. 497-503.

Series 5000 Model XTF5011 X-Ray Tube Information, Oxford Instruments Inc., Scotts Valley, GA, U.S.A., Jun. 1998.

J.M. Leng, et al., "Simultaneous measurement of six layers in a silicon on insulator film stack using spectrophotometry and beam profile reflectometry", J. Appl. Physics 81(8), Apr. 1997.

R. Levine Parrill, et al, "GISAXS—Glancing Incidence Small Angle X-ray Scattering", Journal de Physique IV 3 (Dec. 1993), pp. 411-417.

F. Neissendorfer, et al., "The energy-dispersive reflectometer/diffractometer at BESSY-I", Meas. Sci. Technol. 10 (1999), 354-361.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Chihab et al., "New Apparatus for Grazing X-Ray Reflectometry in the Angle-Resolved Dispersive Mode", Journal of Applied Crystallography 22 (1989), p. 460.

Doubly-Bent Focusing Crystal Optic, Produced by XOS Inc., of Albany, New York. Jul. 2000.

An English abstract of JP 09 308339, Dec. 2, 1997.

Model S7032-0908N array, Produced by Hamamatsu, of Hamamatsu City, Japan. May 2000.

U.S. Appl. No. 60/753,895, filed Dec. 22, 2005.

U.S. Appl. No. 60/800,589, filed May 15, 2006.

An English abstract of JP 10 048398, Feb. 20, 1998.

* cited by examiner

US 7,649,978 B2

AUTOMATED SELECTION OF X-RAY REFLECTOMETRY MEASUREMENT LOCATIONS

CROSS-REFERENCE TO RELATED APPLICATION

This application is a continuation of U.S. Patent application Ser. No. 11/798,617 filed May 15, 2007 now abandoned, which claims the benefit of U.S. Provisional Patent Application 60/800,589, filed May 15, 2006, both of which is applications are incorporated in their entirety herein by reference.

FIELD OF THE INVENTION

The present invention relates generally to X-ray reflectometry (XRR), and particularly to methods and systems for thin film analysis using X-rays.

BACKGROUND OF THE INVENTION

X-ray reflectometry (XRR) is a well-known technique for measuring the thickness, density and surface quality of thin film layers deposited on a substrate. X-ray reflectometers typically operate by irradiating an area on the surface of a sample with a beam of X-rays at grazing incidence, i.e., at a small angle relative to the surface of the sample, near the total external reflection angle of the sample material. Measurement of X-ray intensity reflected from the sample as a function of angle gives a profile of interference fringes, referred to as an XRR spectrum. Properties of the sample layers can be estimated by analyzing the XRR spectrum. Several X-ray reflectometers have been described in the patent literature, such as in U.S. Pat. Nos. 6,512,814, 5,619,548 and 5,923,720, whose disclosures are incorporated herein by reference.

XRR is sometimes used for inspecting patterned wafers. For example, U.S. Pat. No. 6,754,305, whose disclosure is incorporated herein by reference, describes XRR methods for measuring the thickness of thin films on patterned semiconductor wafers in which the feature size is smaller than the measurement spot.

XRR may also be used for in situ inspection, i.e., during the deposition of thin film layers on a wafer. Such a system is described, for example, in U.S. Patent Application Publication 2001/0043668 A1, whose disclosure is incorporated herein by reference. A deposition furnace is provided with X-ray incidence and extraction windows in its side walls. The substrate upon which the thin film has been deposited is irradiated through the incidence window, and the X-rays reflected from the substrate are sensed through the X-ray extraction window.

SUMMARY OF THE INVENTION

When a sample, such as a semiconductor wafer, is inspected using XRR, the measured XRR spectrum is often affected by the presence of surface features, such as conductor patterns and pads, in the irradiated area. In many practical applications, it is desirable to avoid such surface features and select the location of the irradiated area so that the measured spectrum truly represents the layer properties of the sample. Manual evaluation and selection of appropriate irradiation locations is a lengthy, time-consuming process which requires skill and is prone to human errors.

In view of these difficulties, embodiments of the present invention provide methods and systems for automated selection of XRR irradiation locations on the surface of a sample.

In the methods and systems described herein, a set of potential locations on the surface of the sample is defined. At each of these locations, the surface is irradiated with a beam of X-rays and the resulting X-ray spectrum is measured. The X-ray spectra measured at the different potential locations is analyzed to produce respective figures-of-merit indicative of the measurement quality of the spectrum at each location. One or more locations having the best figures-of-merit are selected, and the sample properties are estimated using the X-ray spectra measured at the best-performing locations.

In many cases, high-quality X-ray spectra are characterized by deep, well-defined interference fringes. X-ray spectra distorted by surface features, on the other hand, often have shallower, less distinct fringes. The depth and definition of the fringes, in other words, are indicative of the quality of the information provided by a particular spectrum. Thus, in some embodiments, the figure-of-merit used for evaluating the X-ray spectra comprises the overall length of the X-ray spectrum curve. Exemplary test results that use the curve-length figure-of-merit are shown and discussed below.

Since the methods and systems described herein enable automated, rapid selection of irradiation locations, they are particularly suitable for use in real-time applications, such as detecting process faults and estimating process parameters in the fabrication process of semiconductor wafers. Exemplary wafer fabrication systems that use these methods are described hereinbelow.

The present invention will be more fully understood from the following detailed description of the embodiments thereof, taken together with the drawings in which:

DETAILED DESCRIPTION OF EMBODIMENTS

XRR System Description

Figure 1:
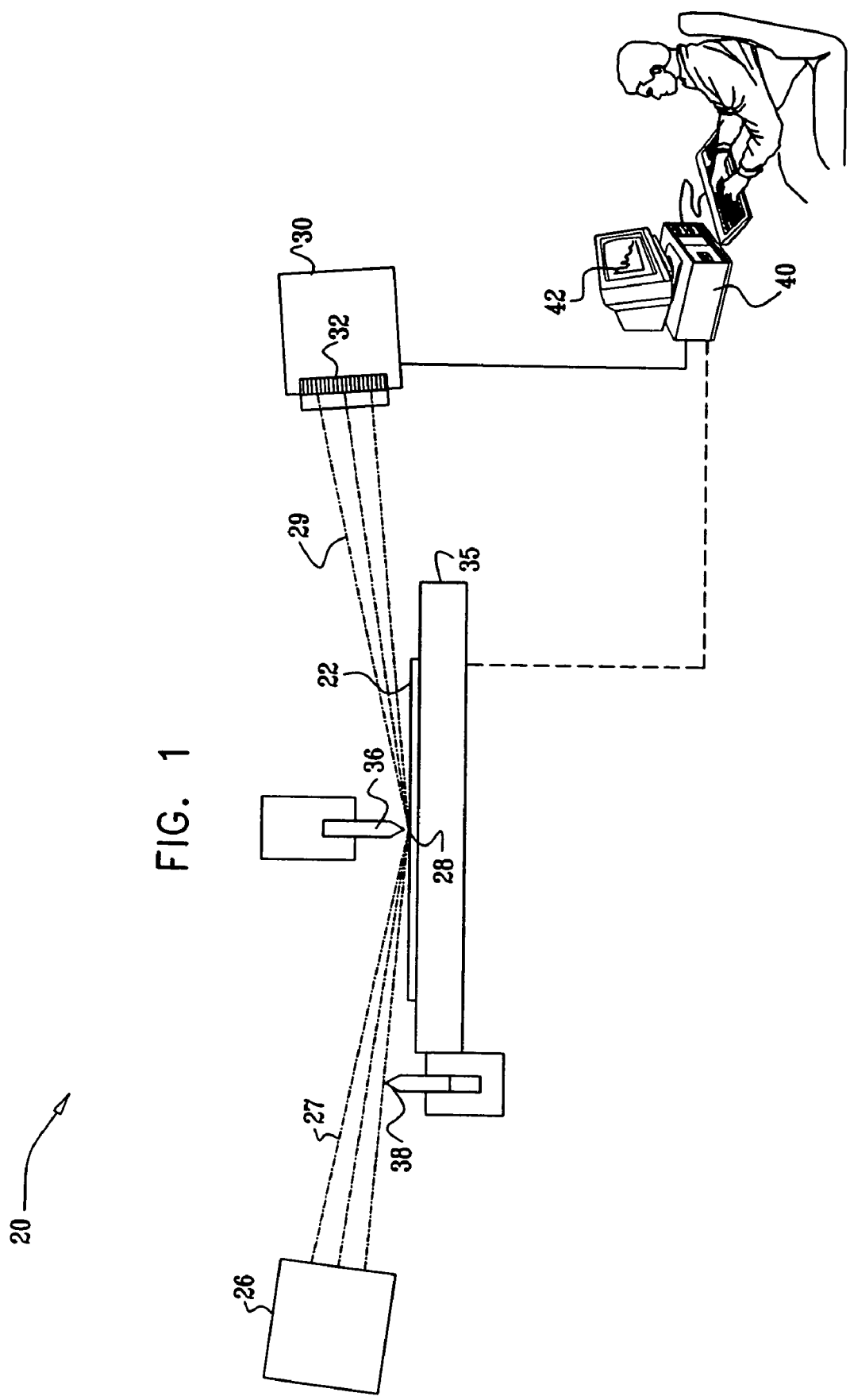
FIG. 1 is a schematic illustration of a system for X-ray reflectometry, in accordance with an embodiment of the present invention.

FIG. 1 is a schematic illustration of a system 20 for X-ray reflectometry (XRR) of a sample, such as a semiconductor wafer 22, in accordance with an embodiment of the present invention. System 20 can be used, for example, in a semiconductor fabrication facility, for identifying process faults and estimating process parameters at different stages of the wafer production process. Two exemplary applications are described in FIGS. 6 and 7 below.

An X-ray source 26 irradiates a small area 28 at a particular location on wafer 22. A dynamic knife edge 36 and a shutter 38 may be used to limit an incident beam 27 of the X-rays. Typically, area 28 has a diameter on the order of 50-100 microns, although other area sizes can also be used. A reflected beam 29 of X-rays from wafer 22 is collected by a detector assembly 30. Typically, assembly 30 collects reflected X-rays over a range of reflection angles between about 0° and 5°, both below and above the critical angle of the wafer for total external reflection. Assembly 30 comprises a detector array 32, typically arranged in either a linear or a matrix (two-dimensional) array.

System 20 can position irradiated area 28 at different locations on the surface of wafer 22. In the exemplary embodiment of FIG. 1, wafer 22 is mounted on a computer-controlled motion stage 35 that allows, inter alia, accurate positioning of the irradiated area. Alternatively, wafer 22 may be static and source 26 and assembly 30 may be set in motion to position area 28 at any desired location on the surface. Further alternatively, any other mechanism can be used to control the location of irradiated area 28 on the surface of wafer 22.

Figure 5:
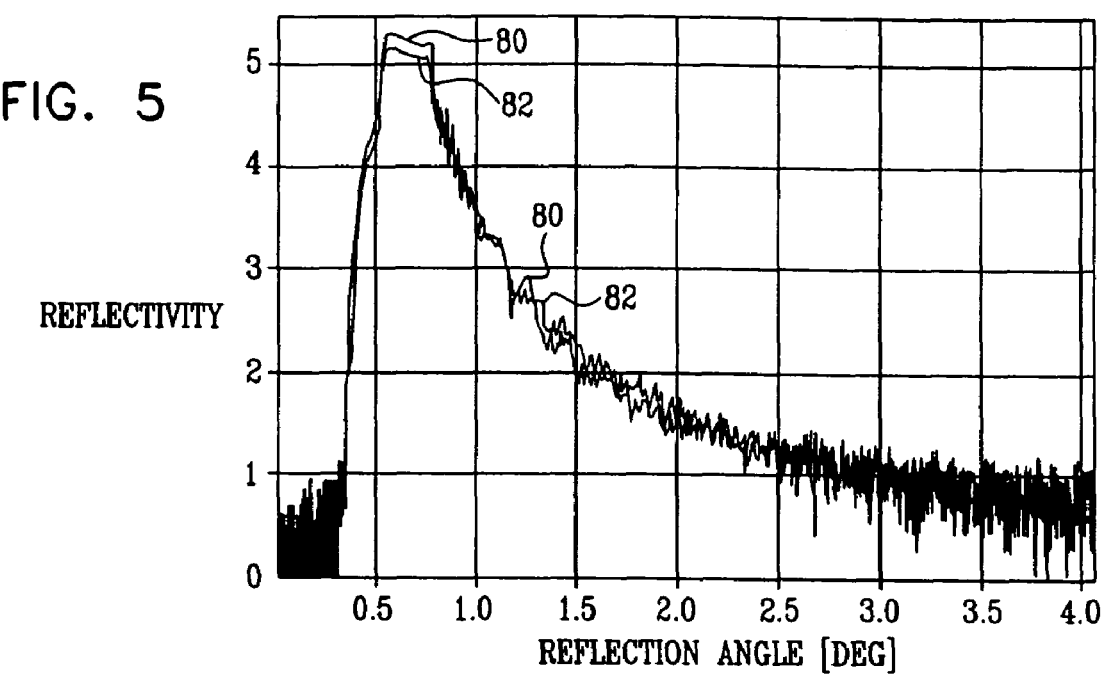
FIG. 5 is a graph showing XRR spectra, in accordance with an embodiment of the present invention.

A reflectometry processor 40 analyzes the output of assembly 30, so as to determine an X-ray spectrum comprising an interference profile 42 of the flux of X-ray photons reflected from wafer 22 as a function of angle. The X-ray spectrum is also referred to as an X-ray reflectometry (XRR) spectrum. Typically, wafer 22 has one or more thin surface layers, such as thin films, at area 28, so that interference profile 42 exhibits an oscillatory structure due to interference effects among reflected X-ray waves from the interfaces between the layers. Exemplary XRR spectra are shown in FIG. 5 below.

Processor 40 analyzes the measured XRR spectrum in order to estimate properties of wafer 22, such as the thickness, density and surface roughness of different layers. The estimated properties can be compared with expected or specified values defined for the wafer. Deviation from the expected values may indicate a manufacturing fault. Several methods are known in the art for calculating sample properties based on a measured XRR spectrum. Some of these methods involve fitting a parametric layer model to the measured results using an optimization process. Exemplary methods are described in the above-cited references. Processor 40 may use any suitable estimation method for this purpose.

The exemplary XRR system of FIG. 1 is shown purely for the sake of conceptual clarity. The methods described herein can alternatively be used in any other suitable XRR system, such as the X-ray reflectometers described in the above-cited references.

Typically, processor 40 comprises a general-purpose computer processor, which performs the functions described hereinbelow under the control of suitable software. The software may be downloaded to the processor in electronic form, over a network, for example, or it may alternatively be provided on tangible media, such as optical, magnetic or non-volatile electronic memory. Further alternatively, the functions described hereinbelow may be implemented in dedicated hardware logic, or using a combination of hardware and software elements.

Reflectometry processor 40 may be implemented as a standalone unit, or it may alternatively be integrated with a semiconductor production and/or test equipment setup or other platform. Further alternatively, the functions of processor 40 may be distributed among several separate computing platforms.

Selection of XRR Measurement Location

In many practical cases, different locations on the surface of a thin film layer on wafer 22 produce different XRR spectra. In other words, if irradiated area 28 falls at different locations on the surface of the wafer, different XRR spectra may be measured. Typically, some locations produce high-quality XRR spectra that are clearly indicative of the layer structure of the wafer, while other locations produce distorted, lower-quality spectra.

For example, in some embodiments the inspected wafer is patterned, having conductors, pads or other features disposed on its surface. Different surface features within the irradiated area typically distort the XRR spectrum. The measured XRR spectrum may vary from one location to another due to differences caused by surface features and/or by features in inner layers. For example, in patterned wafers, scribe lines defining boundaries between neighboring dies are sometimes selected as possible locations for performing XRR measurements. In many practical cases, however, scribe lines are not completely clear of conductors, such as alignment marks, test pads and other features.

As noted above, the measured XRR spectrum is subsequently used by processor 40 as a basis for modeling and/or estimation of the wafer layer properties. For this purpose, it is important to obtain measured XRR spectra that are not distorted by surface artifacts, such as the surface features described above. Thus, it is desirable to select one or more locations on the surface of wafer 22, so that the XRR spectrum measured at these locations is least affected by surface features and other location-dependent effects. Measuring the XRR spectrum at these selected locations enhances the information content of the measured spectrum and improves the confidence that the measured spectrum reliably represents the true layer structure of the wafer, thereby significantly improving the modeling and estimation accuracy of the layer properties.

In some cases, the location selection process may be performed manually. For example, XRR spectra can be measured at several potential locations. The quality of the measured spectra is then evaluated visually by a skilled user, based on past experience and possibly acquired heuristics, to select the appropriate irradiation location. Such a manual process is inherently an off-line process, which is time-consuming, prone to human errors and requires a high level of skill and experience.

In many applications, however, it is necessary to perform the location selection process rapidly. For example, when sample inspection is part of a wafer fabrication process, wafers should be inspected quickly enough so as not to slow down the throughput of the process. In such applications, manual selection of irradiation locations is typically not feasible. In other applications, it is desirable to rapidly narrow down the number of potential locations and present to a user a relatively small and manageable number of suggested locations, which are then evaluated manually.

Embodiments of the present invention thus provide automated (i.e., automatic or semi-automatic) methods and systems for selecting irradiation locations for XRR measurements on the wafer surface. In principle, multiple potential locations on the wafer surface are defined. System 20 measures the XRR spectrum at each potential location. For each measured XRR spectrum, processor 40 calculates a pre-defined figure-of-merit, which is indicative of the measurement quality of the spectrum. The location or locations having the best figures-of-merit are selected. For example, a figure-of-merit that can be used for evaluating XRR spectra comprises the overall length of the spectrum curve, as described below.

Figure 2:
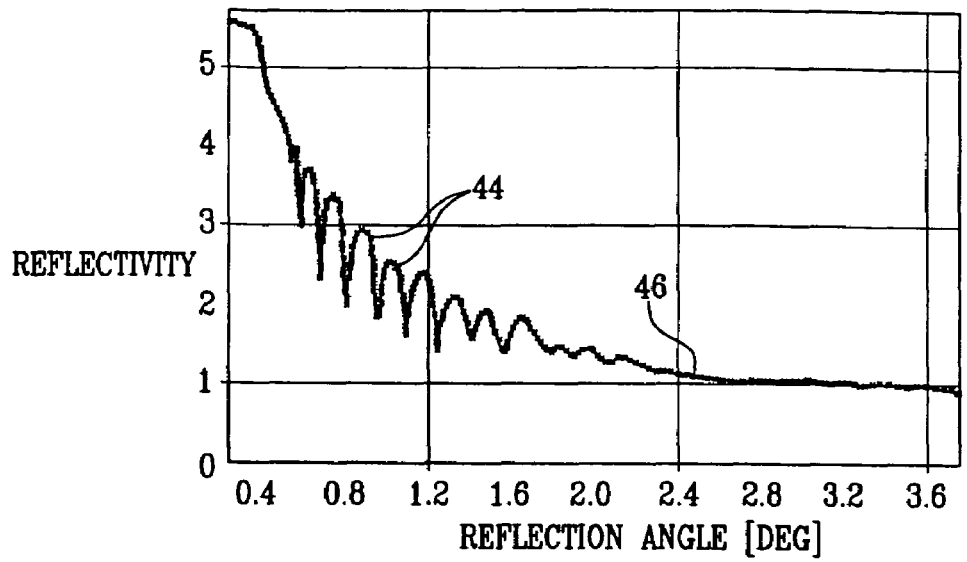
FIG. 2 is a graph showing an XRR spectrum, in accordance with an embodiment of the present invention.

FIG. 2 is a graph showing an exemplary measured XRR spectrum, in accordance with an embodiment of the present invention. The graph shows multiple data points 44 measured by system 20. Each data point 44 shows the measured reflectivity, on a logarithmic scale, at a particular reflection angle.

As can be seen in the figure, the spectrum has an oscillatory nature, showing deep, distinct periodic fringes, as a result of interference between reflections of the X-ray beam from the different layer surfaces.

Extensive experimentation shows that there is often a direct relationship between the depth of the oscillation fringes in the XRR spectrum and the measurement quality of the spectrum. When the measured XRR spectrum has deep, well defined oscillation fringes, the spectrum tends to represent the layer properties of the wafer accurately and reliably. On the other hand, when surface features and other location-dependent features are present, the oscillation fringes often become shallower, blurred and less defined. The estimation accuracy based on such spectra is typically degraded.

The distinctiveness and particularly the depth of the oscillation fringes in the XRR spectrum can be quantified by measuring the overall length of the spectrum curve. Deep fringes will typically produce a longer curve, and vice versa. For example, in some embodiments processor 40 interpolates or otherwise fits a curve 46 to data points 44. The overall length of curve 46 is then used as a figure-of-merit that is indicative of the measurement quality of the spectrum. Typically, the curve length is measured when the spectrum is laid on a semi-logarithmic scale (i.e., when the logarithm of the reflectivity is plotted against the angle of reflection), thus emphasizing the depth of the weak, higher-order fringes.

Processor 40 can use any suitable method for calculating the length of the spectrum curve based on the measured data points. For example, the processor may calculate the curve length CL using a curvilinear integral formula given by $$CL = \int_{x1}^{x2} dx \sqrt{1 + \left(\frac{d\log(I(x))}{dx}\right)^2}$$

wherein I(x) denotes the intensity of the XRR spectrum at angle x, and x1 and x2 denote the boundaries of the angular range of interest. For a discrete angular range, CL is given by $$CL = \sum_{i=m}^{n} \left|\log\frac{I_{i+1}}{I_i}\right|$$

wherein m and n denote the start and end indices of the angular range, and $I_i$ denotes the intensity at the angle indexed i.

Alternatively, the processor can calculate the length of the spectrum curve by calculating and summing the Cartesian distances between successive data points. Further alternatively, processor 40 can fit a polynomial or other function to the data points and calculate the length of the fitted curve.

Often, the curve length is measured in a partial angular range that is of interest. In FIG. 2, for example, measurements at angles greater than ~2° have a relatively small intensity and have little or no oscillatory content. Thus, measuring the curve length only within the angular range [0,2°] often proves more accurate. The smallest angle in the range is sometimes selected to be the critical angle position (typically the angle at which the intensity is equal to half of the maximal measured value). The largest angle in the range is sometimes selected to be the angle in which the measured intensity drops to a pre-determined threshold, such as 100 counts.

Additionally or alternatively, curve 46 can be filtered or otherwise smoothed to reduce the effect of measurement noise and other statistical fluctuations. Further additionally or alternatively, an intensity threshold can be defined, and data points having intensities (reflectivities) smaller than the threshold can be omitted from the process. In alternative embodiments, processor 40 can use any other suitable figure-of-merit for evaluating the measured XRR spectra.

Figure 3:
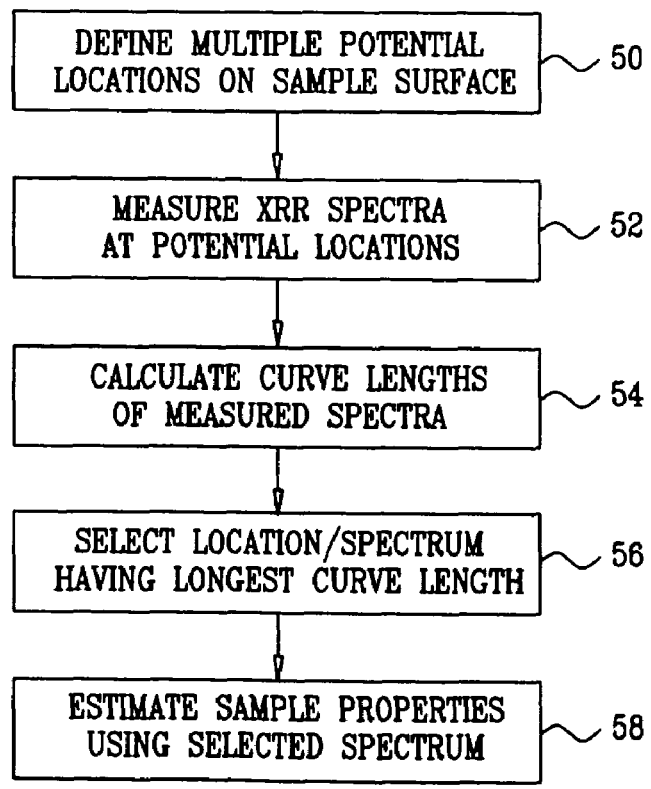
FIG. 3 is a flow chart that schematically illustrates a method for selecting XRR locations on a sample, in accordance with an embodiment of the present invention.

FIG. 3 is a flow chart that schematically illustrates an automated method for selecting XRR locations on wafer 22, in accordance with an embodiment of the present invention. The method begins by defining multiple potential locations on the wafer surface, at a potential location definition step 50.

The potential locations may be defined in advance by a user and provided to processor 40. For example, the user may inspect the wafer visually and attempt to locate clear areas having few or no conductors or other surface features. Potential locations can also be defined based on knowledge regarding the layout of the wafer. For example, when wafer 22 comprises a patterned wafer divided into dies, potential locations may be defined along the scribe lines of the wafer (i.e., the lines defining the boundaries between adjacent dies on the wafer). The scribe lines are normally kept clear of conductors, and thus may serve as good potential candidates for measurement locations.

In some embodiments, potential locations may be suggested automatically by applying an automatic pattern recognition process. In other words, an optical image of the wafer can be analyzed using a suitable pattern recognition method to identify potentially clear areas. Additionally or alternatively, any other manual or automated method can be used to define potential locations for XRR measurements and provide the potential locations to processor 40.

System 20 measures XRR spectra at the potential locations, at a measurement step 52. System 20 scans through the different potential locations and measures the XRR spectrum at each potential location. In the embodiment of FIG. 1 above, processor 40 controls motion stage 35 so as to move the location of irradiated area 28 on the wafer surface. In some embodiments, the system may acquire and average two or more spectra at a particular potential location, in order to reduce measurement errors.

In some embodiments, processor 40 normalizes the XRR spectra measured at the potential locations with respect to one another, e.g., by normalizing the spectra with respect to the first spectrum in the set. Normalization typically comprises intensity (vertical scale) and angular shift (horizontal scale) adjustment. In some embodiments, normalizing the spectra on a logarithmic scale reduces the uncertainty of the normalization factor.

Processor 40 calculates the spectrum curve length of the XRR spectrum measured at each potential location, at a figure-of-merit calculation step 54. As noted above, any suitable method can be used to calculate the curve length, such as summing the Cartesian distances between successive data points. In alternative embodiments, a different figure-of-merit can be used.

Processor 40 then selects the location whose XRR spectrum has the longest curve, at a selection step 56. In some embodiments, two or more locations may be selected. For example, processor 40 may be configured to select a pre-defined number of locations having the longest curves, or all locations whose curve lengths exceed a certain threshold. Having selected one or more locations out of the potential locations, processor 40 estimates the sample properties based on the XRR spectra measured at the selected locations, at a property estimation step 58.

The method of FIG. 3 can be used in different ways in different applications and processes. For example, processor 40 can operate in a fully-automatic mode, accepting a set of potential locations, selecting the best performing location out of the set, and estimating the wafer properties based on the XRR spectrum at the selected location. As another example, processor 40 may operate in a semi-automatic mode, accepting a set of potential locations and reducing them to a smaller set of suggested locations, based on figure-of-merit calculation. The XRR spectra at the suggested locations are then examined by a user who selects the best-performing location.

When multiple wafers are being inspected, such as in a production line, some of the method steps may be performed off-line, only once or only occasionally, while other steps may be performed for every wafer. For example, the definition of the potential locations may be performed only once for a given wafer design. Then, the selection of best-performing locations out of the potential locations can be carried out specifically for each inspected wafer.

EXPERIMENTAL RESULTS

The method of FIG. 3 above was applied to a patterned copper/tantalum wafer. Forty-five potential locations, denoted #1 . . . #45, were defined along a scribe line of the wafer, and the XRR spectrum was measured at each of these locations. The measurements were performed using a JVX 5100 X-ray reflectometer produced by Jordan Valley Semiconductors, Inc. (Austin, Tex.).

Figure 4:
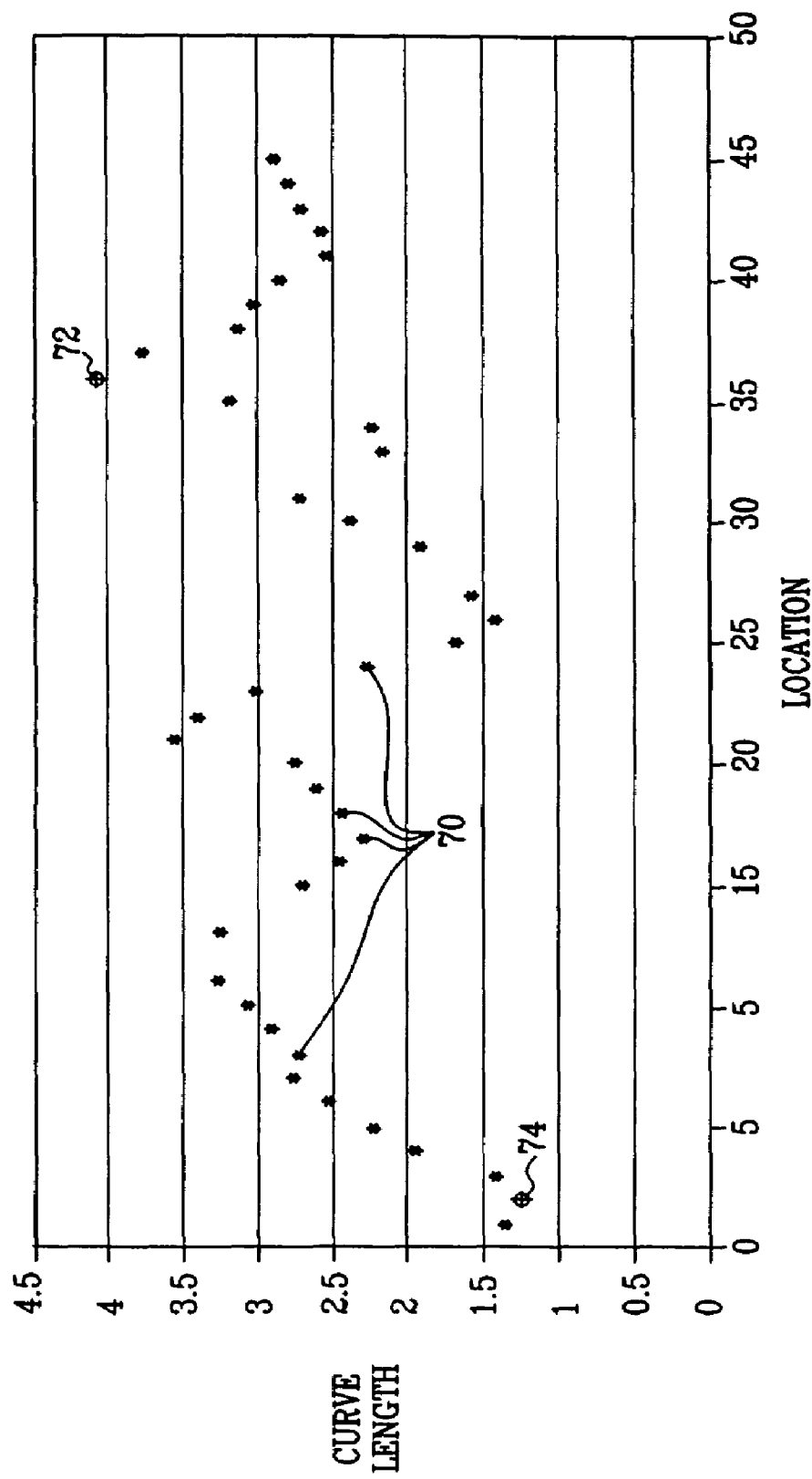
FIG. 4 is a graph showing curve lengths of XRR spectra, in accordance with an embodiment of the present invention.

FIG. 4 is a graph showing curve lengths of XRR spectra, in accordance with an embodiment of the present invention. Data points 70 show the spectrum curve lengths of the XRR spectra measured at the 45 potential locations. The vertical axis gives the curve length in arbitrary units, enabling the different data points to be compared to one another. A data point 72, corresponding to location #36, has a longest curve length of 4.07. A data point 74, corresponding to location #2, has a shortest curve length of 1.2. Thus, location #36 is selected as the best location for performing XRR measurements out of the 45 potential locations.

FIG. 5 is a graph showing the XRR spectra measured at locations #36 and #2, in accordance with an embodiment of the present invention. A curve 80 shows the XRR spectrum measured at location #36, the selected best performing location. A curve 82 shows the XRR spectrum measured at location #2, the worst performing location out of the 45 potential locations. As can be seen in the figure, the interference fringes in the XRR spectra of curve 80 are deeper and more distinct, in comparison with the fringes of curve 82.

XRR Location Selection in a Wafer Fabrication Process

Figure 6:
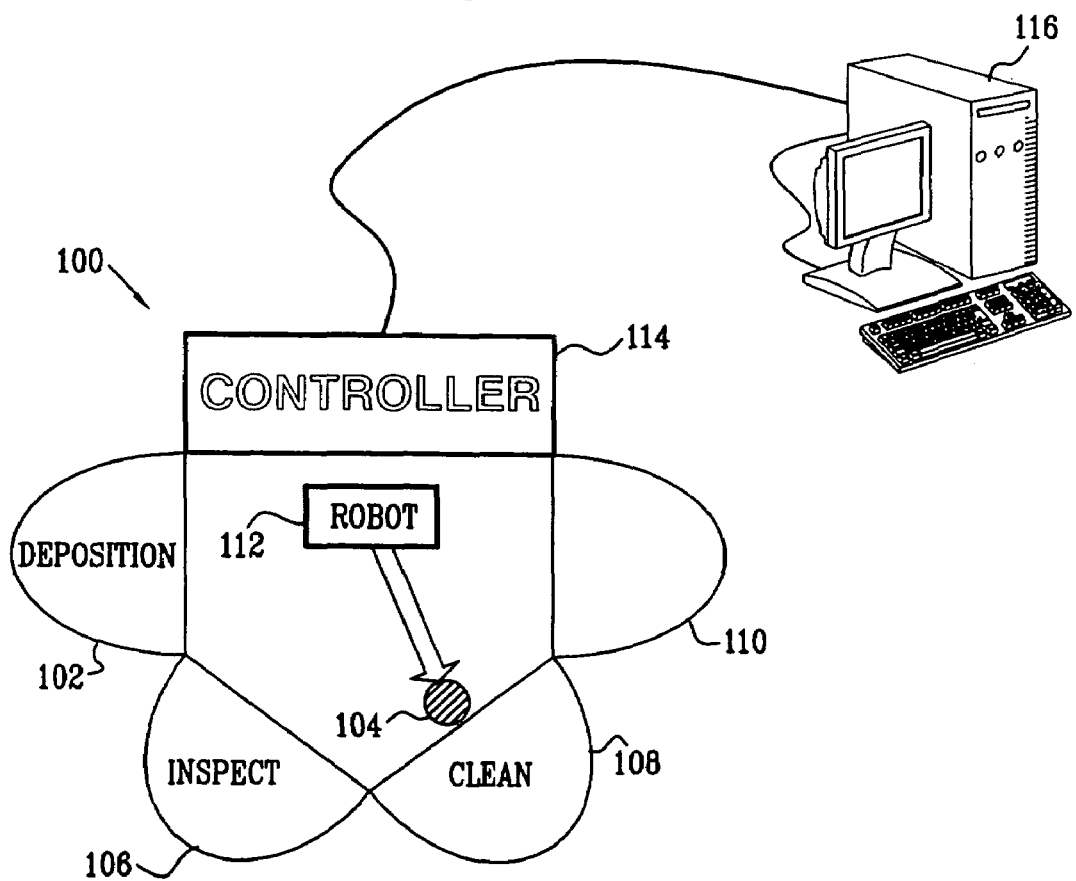
FIGS. 6 and 7 are schematic illustrations showing systems for semiconductor device fabrication, in accordance with embodiments of the present invention.

FIG. 6 is a schematic illustration of a system 100 for use in semiconductor device fabrication, in accordance with an embodiment of the present invention. System 100 comprises a cluster tool having multiple stations, including a deposition station 102 for depositing thin films on a semiconductor wafer 104, an inspection station 106, and other stations 108, 110, as are known in the art, such as a cleaning station. Inspection station 106 is constructed and operated in a manner similar to system 20, as described hereinabove. A robot 112 transfers wafer 104 among the different stations under the control of a system controller 114. The operation of system 100 may be controlled and monitored by an operator using a workstation 116, coupled to controller 114.

Inspection station 106 is used to perform X-ray inspection of wafers by XRR. Such inspection is typically carried out before and/or after selected steps in production processes carried out by deposition station 102 and other stations in system 100. In particular, inspection station 106 performs automated selection of XRR locations on the surface of wafer 104 using the methods described above. The use of station 106 allows early detection of process deviations and convenient adjustment and evaluation of process parameters on production wafers, using controller 114 and possibly workstation 116.

Figure 7:
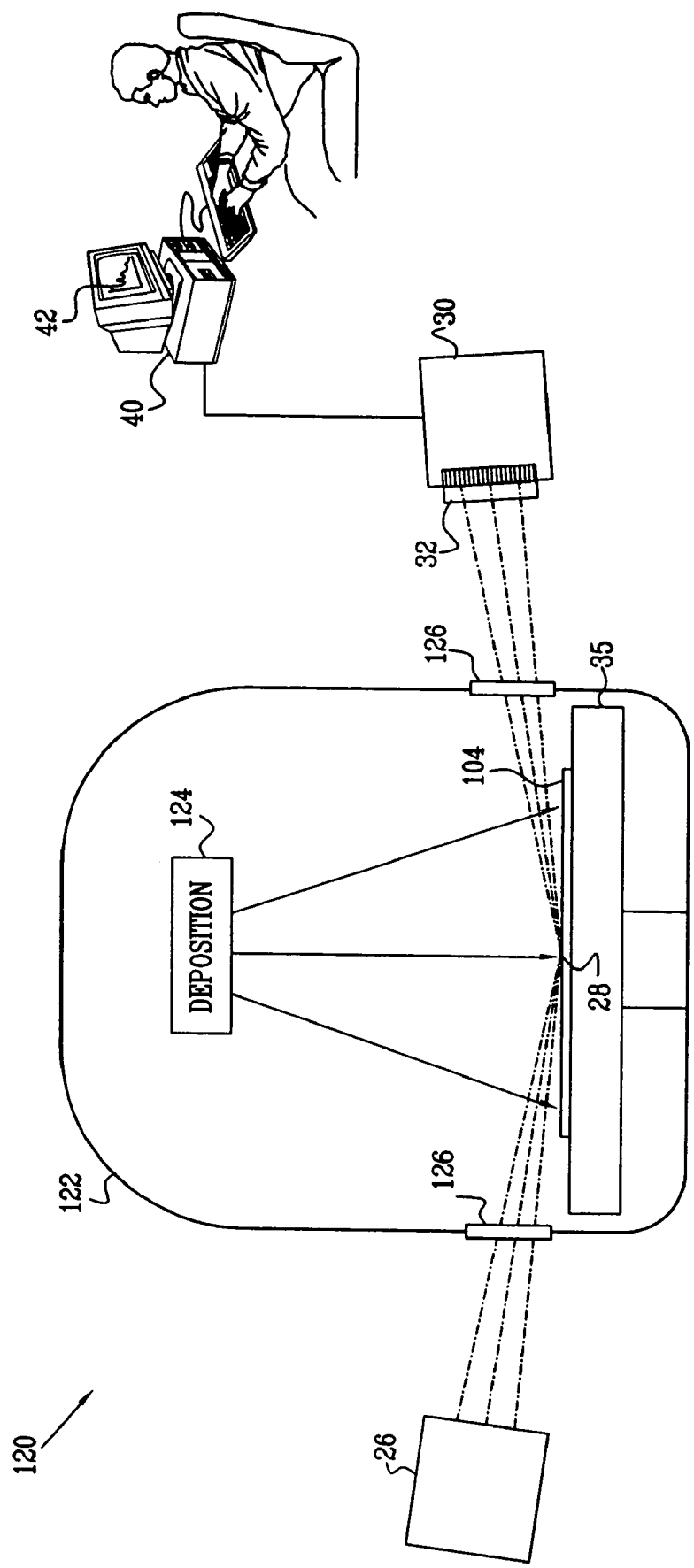

FIG. 7 is a schematic side view of a system 120 for semiconductor wafer fabrication and in situ inspection, in accordance with another embodiment of the present invention. System 120 comprises a vacuum chamber 122, containing deposition apparatus 124, for creating thin films on wafer 104, as is known in the art. The wafer is mounted on motion stage 35 within chamber 122. The chamber typically comprises X-ray windows 126. X-ray source 26 irradiates area 28 on wafer 104 via one of windows 126, in the manner described above. Some of the elements shown in FIG. 1 are omitted from FIG. 7 for the sake of simplicity, but typically, elements of this sort are integrated into system 120, as well.

X-rays reflected from area 28 are received by array 32 in detector assembly 30 via another one of windows 146. Processor 40 receives signals from detector assembly 30 and processes the signals in order to assess characteristics of thin-film layers in production within chamber 122, by measuring the XRR spectrum of wafer 104. In particular, system 120 performs automated selection of XRR locations on the surface of wafer 104 in the manner described above. The results of the XRR assessment may be used in controlling deposition apparatus 124 so that the films produced by system 120 have desired characteristics, such as thickness, density, composition and surface roughness.

Although the embodiments described herein mainly address automated location selection in XRR systems, the principles of the present invention can also be used for selecting measurement locations in other systems that make angle-resolved scattering measurements from a sample surface. Furthermore, the methods and systems described herein can be used in conjunction with other techniques for selection of optimal measurement locations, such as techniques based on optical microscopy (bright field and/or dark field), X-ray fluorescence (XRF), or signals received from focus electronics (which are sensitive to target surface reflection, material and interference effects).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A computer-implemented method for inspection of a sample, comprising:
defining a plurality of locations on a surface of the sample;
irradiating the surface at each of the locations with a beam of X-rays and measuring an angular distribution of the X-rays that are emitted from the surface responsively to the beam, so as to produce a respective plurality of X-ray spectra;
analyzing the X-ray spectra to produce respective figures-of-merit indicative of a measurement quality of the X-ray spectra at the respective locations;
selecting one or more locations out of the plurality of locations responsively to the figures-of-merit; and estimating a property of the sample using the X-ray spectra measured at the selected locations.

2. The method according to claim 1, wherein the sample comprises a semiconductor wafer, and wherein estimating the property comprises at least one of detecting a fault and estimating a process parameter in a fabrication process of the semiconductor wafer.

3. The method according to claim 1, wherein the figures-of-merit comprise a measure of information content of the X-ray spectra.

4. The method according to claim 3, wherein the measure of the information content comprises curve lengths of the respective X-ray spectra with the X-ray spectra expressed as reflectively values as a function of reflection angle.

5. The method according to claim 4, wherein analyzing the X-ray spectra comprises calculating the curve lengths using a curvilinear formula.

6. The method according to claim 4, wherein the X-Ray spectra are expressed as logarithms of the reflectivity values as a function of reflection angle.

7. The method according to claim 1, wherein analyzing the X-ray spectra comprises at least one of pre-filtering the X-ray spectra and omitting from the X-ray spectra data points having reflectivities smaller than a predetermined threshold.

8. The method according to claim 1, wherein defining the plurality of locations comprises at least one of accepting a definition of the locations from a user and determining the locations using an automatic pattern recognition process.

9. The method according to claim 1, wherein the sample comprises a patterned wafer, and wherein defining the plurality of locations comprises positioning at least some of the locations on a scribe line of the wafer.

10. Apparatus for inspection of a sample, comprising:
an X-ray source, which is arranged to irradiate a surface of the sample with a beam of X-rays at a plurality of locations on the surface;
a detector assembly, which is arranged to measure a distribution of the X-rays that are emitted from the plurality of the locations responsively to the beam, so as to produce a respective plurality of X-ray spectra; and
a processor, which is arranged to analyze the X-ray spectra to produce respective figures-of-merit indicative of measurement quality of the X-ray spectra at the respective locations, to select one or more locations out of the plurality of locations responsively to the figures-of-merit, and to estimate a property of the sample using the X-ray spectra measured at the selected locations.

11. The apparatus according to claim 10, wherein the sample comprises a semiconductor wafer, and wherein the processor is arranged to perform at least one of detecting a fault and estimating a process parameter in fabrication process of the semiconductor wafer by estimating the property.

12. The apparatus according to claim 10, wherein the figures-of-merit comprise a measure of information content of the X-ray spectra.

13. The apparatus according to claim 12, wherein the measure of the information content comprises curve lengths of the respective X-ray spectra with the X-ray spectra expressed as reflectivity values as a function of reflection angle.

14. The apparatus according to claim 13, wherein the processor is arranged to calculate the curve lengths by applying a curvilinear formula.

15. The apparatus according to claim 13, wherein the X-ray spectra are expressed as logarithms of the reflectivity values as a function of reflection angle.

16. The apparatus according to claim 10, wherein the processor is arranged to perform at least one of pre-filtering the X-ray spectra and omitting from the X-ray spectra data points having reflectivities smaller than a predetermined threshold.

17. The apparatus according to claim 10, wherein the processor is arranged to determine the plurality of locations using an automatic pattern recognition process.

18. The apparatus according to claim 10, wherein the sample comprises a patterned wafer, and wherein at least some of the locations in the plurality are located on a scribe line of the wafer.

19. A cluster tool for producing microelectronic devices, comprising:
a deposition station, which is arranged to form a thin-film layer on a surface of a semiconductor wafer; and
an inspection station, comprising:
an X-ray source, which is arranged to irradiate the surface of the semiconductor wafer with a beam of X-rays at a plurality of locations on the surface;
a detector assembly, which is arranged to measure a distribution of the X-rays that are emitted from the plurality of the locations responsively to the beam, so as to produce a respective plurality of X-ray spectra; and
a processor, which is arranged to analyze the X-ray spectra to produce respective figures-of-merit indicative of a measurement quality of the X-ray spectra at the respective locations, to select one or more locations out of the plurality of locations responsively to the figures-of-merit, and to estimate a property of the thin-film layer using the X-ray spectra measured at the selected locations.

20. Apparatus for producing microelectronic devices, comprising:
a production chamber, which is arranged to receive a semiconductor wafer;
a deposition device, which is arranged to deposit a thin-film layer on a surface of the semiconductor wafer within the chamber;
an X-ray source, which is adapted to irradiate the surface of the semiconductor wafer in the production chamber with a beam of X-rays at a plurality of locations on the surface;
a detector assembly, which is arranged to measure a distribution of the X-rays that are emitted from the plurality of the locations responsively to the beam, so as to produce a respective plurality of X-ray spectra; and
a processor, which is arranged to analyze the X-ray spectra to produce respective figures-of merit indicative of a measurement quality of the X-ray spectra at the respective locations, to select one or more location out of the plurality of locations responsively to the figures-of-merit, and to estimate a property of the thin-film layer using the X-ray spectra measured at the selected locations.

* * * * *